United States Patent [19]

Thakur

[11] 4,443,426

[45] Apr. 17, 1984

[54] BLOOD AGENT

[75] Inventor: Madhukar L. Thakur, Hamden, Conn.

[73] Assignee: Yale University, New Haven, Conn.

[21] Appl. No.: 387,731

[22] Filed: Jun. 14, 1982

[51] Int. Cl.$^3$ .................... A61K 43/00; A61K 49/00
[52] U.S. Cl. ........................................ 424/1.1; 424/9;
260/429 R
[58] Field of Search ................................ 424/1, 1.5, 9; 260/429 R

[56] References Cited

U.S. PATENT DOCUMENTS

| | | | |
|---|---|---|---|
| 3,988,429 | 10/1976 | Richards et al. | 424/1 |
| 4,300,569 | 11/1981 | Bonneau | 424/1 |
| 4,313,928 | 2/1982 | Kato et al. | 424/1.5 |
| 4,335,095 | 6/1982 | Kelly | 424/1 |
| 4,342,740 | 8/1982 | Narra et al. | 424/1.5 |
| 4,348,375 | 9/1982 | Goedemans | 424/1 |
| 4,372,294 | 2/1983 | Strauss et al. | |

OTHER PUBLICATIONS

Scheffel, et al., J. Nucl. Med., 23(2):149–156, 1982.
Dewanjee, et al., J. Nucl. Med., 22(11):981–987, 1981.
Mathias et al., Int. J. Appl. Rad. Isotopes, 32(9)651–656 (1981).
Oberhausen, Chem. Abstracts., 96(5), 1982, #30895v.

*Primary Examiner*—Christine M. Nucker
*Attorney, Agent, or Firm*—Jon S. Saxe; George M. Gould; William H. Epstein

[57] ABSTRACT

An agent for labelling blood cells using a radioactive complex of a radioactive metal with an N-oxide of pyridine which labelled blood cells are useful for in vivo imaging of blood cells for diagnostic purposes.

36 Claims, No Drawings

BLOOD AGENT

BACKGROUND OF INVENTION

The importance of cellular blood elements, such as red cells, platelets, and white cells in health and disease has been long recognized. Associated with every organic illness is an involvement of blood cells. Over the past 25 years, interest in blood cells has intensified and the new and multidisciplinary science of cell pathology has emerged. Advances in optical and cell separation techniques, tissue culture and in the knowledge of cell function have made possible to categorize diseases and identify the type of blood cells involved. These have provided a sound basis for studies with radiolabeled blood cells enabling radiologists to identify and localize abnormal lesions, deep in the body, by gamma camera imaging. The use of radiolabeled blood cells, also has potential to enable investigators to better understand the in vivo cell kinetics and pathophysiology of human diseases.

In 1976, McAfee and Thakur (J. Nucl. Med. 17, 480-487) observed several radioactive agents and concluded that indium-111 chelated to 8-hydroxyquinoline (oxine) provides a best radioactive tracer for cellular blood elements. Indium-111 (In-111) is a commercially available, cyclotron produced radionuclide. The half-life (67 hours) and the gamma rays (173 kev and 247 kev) of the radionuclide are well suited for in vivo applications and gamma camera imaging. The short half-life minimizes the radiation dose to a patient and the gamma ray energies are efficiently detected by the gamma camera. The chelation of In-111 with oxine provides a neutrally charged compound that passively diffuses through cell membrane and the radioactivity binds to a desired type of blood cell without affecting the cell viability. See Thakur, J. Nucl. Med. 18:1022 (1977). However, indium-111 oxine, has characteristics, that lead to a number of disadvantages.

The insolubility of oxine in aqueous solvents necessitates the chelating agent to be dissolved in ethanol before adding to the $^{111}InCl_3$ solution in acetate buffer and requires the resultant lipid soluble complex to be extracted in a nonpolar solvent. If the complex is not extracted, oxine, in the aqueous system, may form a colloid during storage and prevent the radioactive tracer from diffusing across the cell membrane. The nonpolar solvent containing the extracted complex must be evaporated and the complex dissolved in absolute ethanol before being used for cell labeling. Fifty ul of ethanol is used to dissolve 1 mCi $^{111}$In-oxine, since a large quantity of the solvent may be toxic to cells. Some investigators have considered this volume to be too inconvenient for dispensing into several test tubes containing cell suspensions.

The disadvantages of more serious consequences arise from the fact that $^{111}$In-oxine has only moderate thermal stability. Therefore, when $^{111}$In-oxide is added to plasma the major proportion of $^{111}$In-oxine immediately binds to the protein transferrin and thereby severely inhibits the ability of the agent to label cells. This necessitates the cells to be suspended in a nonplasma medium for efficient incorporation of radioactivity.

Although the suspension of erythrocytes, neutrophils, and lymphocytes in a nonplasma medium for efficient $^{111}$In labeling does not reportedly result in any apparent loss of cell viability, the suspension of human platelets in normal saline severely reduces platelet aggregability and in vivo survival.

Thakur et al. in J. Nucl. Med. 22, 381-385, (1981) recently demonstrated that modified Tyrode's solution is a better medium than normal saline for $^{111}$In platelet labelling. Yet, suspension of human platelets even in this medium reduces their aggregability to 66±15% of those suspended in autologous plasma. This has limited to some extent the clinical use of $^{111}$In labeled platelets. It has been desired to provide a labelling agent which can be used which does not bind blood components such as transferrin and will effectively radioactively label blood cells in plasma to preserve the physiological functions of the cells after labelling.

SUMMARY OF INVENTION

In accordance with this invention, a new agent which is a complex of a radioactive metal selected from the group consisting of indium, technetium, gallium, ruthenium with a compound of the formula:

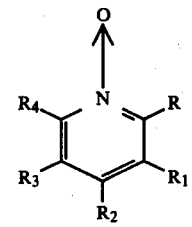

wherein R is an electron donating or an electron withdrawing group; and $R_1$, $R_2$, $R_3$ and $R_4$ are independently hydrogen, methoxy, ethoxy, $-(CH_2)_n-COOH$, methyl, halogen or ethyl; and n is 0 or 1 can be used in imaging blood cells. This radioactive complex can radiolabel blood cells in a plasma media without reacting with the components of the blood such as transferrin to denature or destroy the blood cells into which it is introduced. Furthermore, labelling with the agent of this invention does not adversely affect the in vivo survival of blood cells such as platelets or in any way alter or destroy the physiological function of these cells. The complex of formula I produces radiolabelled blood cells which will accumulate in the desired area to produce accurate imaging for diagnostic purposes.

DETAILED DESCRIPTION

In forming the radioactive metal complex of formula I, any conventional radioactive isotope of indium, technetium, ruthenium or gallium can be utilized. Among the radioactive isotopes are included indium-111, indium-113 m, indium-114 m, indium-109, indium-110, technetium-99 m, ruthenium-97 and gallium-67. The compound of formula I can exist in two forms, among these forms, i.e.

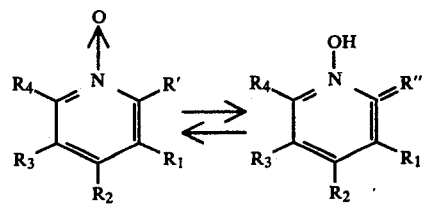

wherein R' is an electron withdrawing or electron donating group with a terminal hydrogen atom and R'' is R' with its terminal hydrogen group removed. The preferred compound of formula I is pyrithione or its alkali metal salts which can exist in two forms, i.e.

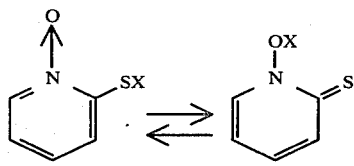

where X is hydrogen or an alkali metal.

The aforementioned radioactive metals can exist with a valence of three and a coordination number of six. Therefore, it is believed that the complex of this invention has the following formula:

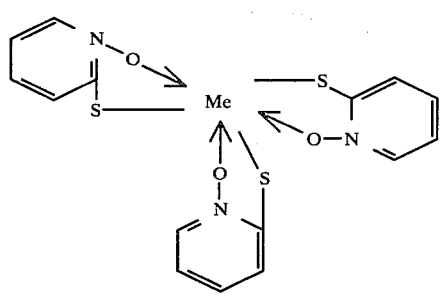

wherein Me is a radioactive metal selected from the group consisting of indium, ruthenium, gallium and technetium. These compounds of formula II are named tris[1-hydroxy-2(1H)pyridinethionato-O,S]radioactive metal.

In the compound of formula I, extensive tests have established the efficacy of the compound where R is —SX and X is hydrogen or alkali metal. However, it is believed that R can comprise other electron withdrawing groups or electron donating groups such as —S$_2$O$_3$, —NH$_2$, —N$_3$, —COOH, —OH, —SH and —CO$_3$. The preferred group is —SX and the preferred compound of formula I is pyrithione and its alkali metal salts such as sodium, potassium and lithium salts.

The complex which can be utilized in imaging blood cells is formed by reacting the compound of formula I with the salt of a radioactive metal. Any conventional salt of these radioactive metals can be used in forming the compound. If one wishes to preform the complex of radioactive technetium with the compound of formula I, one can react technetium-99m pertechnetate with the compound of formula I in the presence of a reducing agent such as stannous chloride so that the technetium is reduced to a valence of 3. On the other hand, radiolabelling can be carried out with the other conventional salts of the radioactive metals of indium, technetium, gallium and ruthenium to produce the complex. Among the other salts are the acetate, citrate and halide salts such as chloride, bromide, fluoride and iodine salts of metals such as indium, ruthenium and gallium in their radioactive form. This reaction to form the complex is carried out by simply mixing the radioactive metal salt with the compound of formula I. This reaction can be carried out in an aqueous medium and at room temperature. In carrying out this reaction, temperature and pressure are not critical and this reaction can be carried out at room temperature and atmospheric pressure. Temperatures as high as 90° C. can be utilized, if desired, in carrying out this reaction. In forming this complex, the radioactive material can have any suitable amount of radioactivity. The radioactivity of this complex will be at least 90% of the radioactivity of the salt of the radioactive metal utilized as the starting material. In forming these radioactive complexes, it is generally preferred to form radioactive complexes containing from about 100 μCi to about 50 mCi, with complexes of from about 0.5 mCi to about 3 mCi being especially preferred. Generally these radioactive complexes are formed in solutions containing radioactive concentrations of from about 0.05 mCi to 100 mCi per ml.

In the next step for preparing as in vivo diagnostic agent for imaging blood cells, the radioactive complex of formula I is reacted with the cells in vitro to radiolabel the cells for administration to the patient. The cell to be labelled can be any of types of cells found in blood. Among these blood cells which can be radiolabelled in accordance with this invention are the platelets, red blood cells and white blood cells such as leukocytes, including neutrophils and lymphocytes or mixtures thereof. The type of cells which are radiolabelled in vitro is dependent upon which of the types of blood cells one wishes to image. If one wishes to image the leukocytes of a patient, one labels with the complex of this invention the leukocytes in vitro for imaging. If one wishes to image the platelets of a patient, one labels the platelets in vitro with the complex of this invention. Generally, it is preferred to radiolabel in vitro blood cells from the same patients in which the diagnostic imaging is to be carried out. On the other hand, one may radiolabel the blood cells taken from a blood donor to image the blood cells of another person. However, in this case, it is preferred that the blood cells be obtained from the same species as to species to be imaged, i.e. for diagnosing human disorders, the blood cells which are labelled by means of the complex of formula I above should be obtained from a human.

Depending upon the disorder to be diagnosed, one utilizes the particular type cells for this disorder. If one wishes to diagnose for internal hemorrhaging or bleeding, one labels the red blood cells with the complex of formula I and injects these radioactive labelled blood cells into the patient to visualize areas of possible bleeding. On the other hand, if one wishes to diagnose for vascular diseases such as thrombosis or platelet clotting, one radioactively labels the platelets and injects these platelets into the patient for detection of these vascular diseases.

If one wishes to diagnose internal infections and inflammations, one labels the white blood cells with the complex of this invention and injects these labelled white cells into the patient for imaging to diagnose for internal infections and inflammations. With respect to lymphocytes, labelling lymphocytes with the complex of formula I provides an agent for imaging for detection of tumors.

The desired blood cells are labelled with the complexing agent of this invention by simply mixing the blood cells with the complex. Generally, it is preferred to carry out this labelling in the presence of plasma. However, any other conventional medium such as saline can also be used as the labelling medium. Generally, it is preferred to carry out this labelling utilizing plasma as the labelling medium. The use of a saline solution or in fact organic solvents may alter and in some cases destroy the physiological functions of a certain cell type to be labelled and therefore these media are less preferred. Therefore, plasma is the preferred medium for labelling. In accordance with this invention, it has been found that the complexing agent of this invention is not deleteriously affected by natural blood proteins such as transferrin. Therefore, one can use plasma as the labelling medium to efficiently effect labelling of the cells.

Radiolabelling is generally carried out by treating from about $0.5 \times 10^8$ cells to about $200 \times 10^8$ cells with the radioactive compound of formula I wherein said radioactive complex has a radioactivity of from 100 $\mu$Ci to about 50 mCi. This reaction can be carried out by simply treating the cells to be labelled with the radioactive complex of formula I in plasma or any other medium such as saline or other salt-balanced solutions. The cells labelled by means of the radioactive metal complex of this invention can be injected intraveneously into a patient for diagnostic imaging. In accordance with this invention, the cells labelled by means of the radioactive metal complex of formula I are administered in a single unit injectable dose. Any of the common carriers such as sterile saline solution, plasma, etc., can be utilized for preparing the injectable solution for use to diagnostically image in accordance with this invention. Generally, the unit dose to be administered contains about $50 \times 10^6$ to about $200 \times 10^8$ labelled blood cells having a radioactivity of about 100 $\mu$Ci to about 50 mCi, preferably 0.5 mCi to 3 mCi. The solution to be injected to unit dosage is from about 0.1 ml to about 10 ml. After intravenous administration, the labelled cells will image the cell in vivo in a matter of a few minutes. However, imaging can take place, if desired, in hours or even longer, after injecting into patients. In most instances, a sufficient amount of the administered dose will accumulate in the area to be imaged within about 0.1 to 10 hours to permit the taking of scintiphotos. Any conventional method of visualizing imaging for diagnostic purposes can be utilized in accordance with this invention.

The cells labelled by means of the radioactive metal complexes of formula I may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred mediums are normal saline and plasma.

The following examples are illustrative but not limitative of the invention:

EXAMPLE 1

Preparation of Indium-111 Chelate of Pyrithione at Various pH's

To several 10 ml iron free glass test tubes were added 2 ml of various buffer solutions having pH's varying from 0.7 to 7.4. A single buffer solution was added to each of the test tubes so that each test contained a given buffer solution at a given pH. Each of these test tubes were utilized to make the indium-111 chelate of pyrithione at different pH's.

To each of the above test tubes were then added 50 $\mu$l of an aqueous solution of pyrithione (concentration 1 mg/ml) containing 0.9% by weight sodium chloride. After this addition, 10 $\mu$l (50 $\mu$Ci) of an aqueous solution containing indium-111 chloride was added to each of these test tubes and the indium-111 complex of pyrithione was produced. A similar number of test tubes treated identically, without the addition of pyrithione, served as controls. The radioactive complex in each of the test tubes was extracted with chloroform and the radioactivity of each of the chloroform extracts containing the indium-111 chelate of pyrithione and the controls was determined. Each of the extracts where pyrithione was added had radioactivity of greater than 45 $\mu$Ci whereas the radioactivity of the extracts from the controls was less than 0.5 $\mu$Ci. Furthermore, there was little difference in the radioactivity of the indium-111 complex formed in the various test tubes at different pH's. These results demonstrated that pH had little influence on the formation of the indium-111 complex of pyrithione.

EXAMPLE 2

Preparation of Indium-111 Complex of Pyrithione

Pyrithione dissolved in saline was mixed in various test tubes with aqueous solutions of 0.1 mCi to 10 mCi indium-111 chloride to form the indium-111 chelate of pyrithione. The pyrithione was added in an amount of 10 $\mu$g for every mCi of indium chloride. The resulting solutions containing this indium 111-chelate of pyrithione were neutralized by adding 0.1 molar aqueous sodium hydroxide. For use in the following examples, the volume of these neutralized solutions containing the complex were adjusted so that the concentration was 1 mCi per ml.

To determine the amount of complex in a 1 ml isotonic saline solution, the isotonic saline solution prepared above containing the complex was extracted twice each with 1 ml of chloroform. The chloroform layer was separated and the radioactivity of the complex in the chloroform layer was determined by means of an ionization chamber. Depending upon the radioactivity of the indium-111 chloride utilized as the starting material, the yield of the complex was determined. The yield was over 90%. If the indium-111 chloride utilized as starting material had radioactivity of 1 mCi, the complex produced had radioactivity of greater than 0.9 mCi. Furthermore, the chloroform extracts of a control prepared by the above procedure without utilizing pyrithione and utilizing indium chloride having a radioactivity of 1 mCi had neglible radioactivity, i.e. less than 0.01 mCi. Therefore, this procedure produces the indium-111 complex of pyrithione, i.e. tris[1-hydroxy-2(1H)pyridine thionato O,S]indium-111 in solution at various radioactivities at a radioactive concentration of about 1 mCi per ml.

EXAMPLE 3

Preparation of Indium-111 Chelate of Pyrithione Concentration

Aqueous indium-111 chloride solution (10 mCi/ml) was evaporated to dryness by heating in a water bath a test tube containing this solution. The resulting residue was dissolved in isotonic saline. To this solution there was added a saline solution of pyrithione (concentration 1 mg per ml). The amount of pyridine that was added was 10 $\mu$g per every mCi of indium-111 chloride. Upon mixing the indium-111 chelate of pyrithione was formed. In this manner, saline solutions of the chelate of various mCi can be prepared depending on the starting mCi of the indium-111 chloride.

EXAMPLE 4

Labelling of Platelets With In-111 Complex in Plasma

Two anticoagulants A and B were prepared as follows:

Solution A(pH 4.5).
5 g of $Na_3C_6H_5O_7 \cdot 2H_2O$
2.9 g of $H_3C_6H_5O_7 \cdot 1H_2O$ The above ingredients were dissolved in 200 ml water to form solution A.

Solution B which had a pH of 4.5 was an aqueous solution containing 3.8% by weight of sodium citrate ($Na_3C_6H_5O_7 2H_2O$).

An amount of 33 ml of blood was drawn in a syringe from a human patient. The syringe contained 7 ml of solution A. The contents of the syringe were divided equally into two 50 ml test tubes both labelled A.

An amount of 15 ml of blood was drawn in a syringe containing 1.5 ml of solution B. The contents of the syringe was placed into a 50 ml test tube. This test tube was centrifuged at 180 g for 15 minutes at a temperature of 22° C. to produce two layers, the top layer being platelet rich plasma (PRP) and the bottom containing red and other blood cells. The top layer (PRP) was separated from the bottom layer and placed in another test tube. From this layer, 0.5 ml PRP was removed and stored for later use as a control. This other test tube containing the PRP was centrifuged at 1,000 g for 15 minutes to produce platelet poor plasma (PPP) and a platelet button which settled at the bottom of the tube. The platelet poor plasma (PPP) was separated and stored for later use.

The test tubes labelled A were centrifuged at 180 g for 15 minutes at 22° C. to produce two layers, the top layer being the platelet rich plasma (PRP) and the bottom being the red and other blood cells. The upper layers of platelet rich plasma were separated from both of the test tubes of solution A and combined in a third test tube. The combined platelet rich plasma layer was centrifuged at 1,000 g for 15 minutes. After centrifugation was completed, the platelets separated out of plasma as a button at the bottom of the test tube within the platelet poor plasma. After centrifugation, all but 1.5 ml of platelet poor plasma was withdrawn from the test tube to leave the button and the 1.5 ml of the platelet poor plasma. The button was dispersed in the platelet poor plasma by mixing.

To this test tube containing the button there was added 500 μl of the isotonic saline solution of indium-111 complex of pyrithione prepared in Example 2 having 500 μCi radioactivity. This mixture was allowed to incubate at room temperature for 15 minutes to allow the indium complex of pyrithione to label the platelets. On the other hand, incubation was also carried out on another sample prepared in the same manner at 37° C. for 10 minutes. After incubation, the test tube was centrifuged. Upon centrifugation, the platelet button separated from the plasma. The radioactivity of both the platelet button and the supernatant plasma was measured. The radioactivity of the button was about 400 μCi. To the platelet button there was added 4 ml of the platelet poor plasma of the control (prepared from Solution B). The radioactive platelet button suspended in the platelet poor plasma was retained for further use.

EXAMPLE 5

Labelling Platelets With Indium-111 Complex In Aqueous Solutions

The platelet button suspended in platelet poor plasma prior to labelling prepared in Example 4 was used in this example. The platelet button was removed from this plasma and suspended in an aqueous solution containing 0.9% by weight sodium chloride. To this suspension in a test tube was added 50 μl of the solution of the complex of pyrithione prepared in Example 2 having 500 μCi radioactivity. The various test tubes that were prepared containing this mixture were either incubated at room temperature for 15 minutes or at 37° C. for 10 minutes. After incubation, the platelets labelled with the indium-111 complex were then centrifuged to obtain the radioactivity labelled button and the supernatant.

EXAMPLE 6

Human platelets were separated and in several test tubes approximately $4 \times 10^8$ cells per ml were placed. The test tubes containing the cells were added at room temperature or at 37° C. to the saline solution containing the complex which was prepared in Example 2 (radioactivity 100 μCi). The test tubes were centrifuged at 1,000×g for 15 minutes. The resulting supernatant was separated, the platelets were washed both with platelet poor plasma and plasma. The radioactivity of the platelets was counted and the percentage associated with the platelets was determined. The results indicated good radioactive labelling efficiency of the platelets at both 37° C. and at room temperature.

EXAMPLE 7

Influence of pH of labelling medium on the labelling of platelet

Platelets were suspended in 0.9% by weight aqueous sodium chloride solution in various test tubes. Each test tube contained approximately $8 \times 10^8$ platelets per milliliter. The pH in each of the test tubes was adjusted to a given value with citric acid or sodium citrate. The pH was 4.46 to 6.96. To each of the test tubes, there was added 100 μl of the indium-111 complex of pyrithione in the saline solution prepared in Example 2. This solution had a radioactivity of 100 μCi. Incubation was carried out at 37° C. for 10 minutes. After the incubation, each of the test tubes were centrifuged to produce the platelet button labeled by means of the indium complex. The radioactivity of each of the platelet buttons were measured. The results indicate that the maximum incorporated radioactivity into the platelets occurs at a neutral pH.

EXAMPLE 8

The platelet survival was carried out on three normal mongrel dogs using the platelets labelled in accordance with Example 4. These labelled platelets suspended in the plasma (4 ml) were then injected intravenously into the respective animals and several blood samples withdrawn at known time intervals for a period of eight days. All of the blood samples were then weighed and the associate radioactivity was counted together with a reference indium 111 solution. Body weights of the animals were recorded to estimate the total blood volume in each animal. From the blood volume and the radioactivity in the sample, the percent of circulating platelets (recovery) was determined on various dogs post injection by the method of Thakur et al., Thrombosis Res., 9, 345 (1976). The percentage of circulating platelets at 5 min. post injection was used as 100%. From this value, the percentage of radioactivity in subsequent blood samples was calculated to determine the platelet's survival. The time for which the labelled platelets remained in circulation was approximately eight days which is the normal life of platelets. Therefore, the procedure of labelling platelets did not alter the physiological effect of the platelets.

EXAMPLE 9

Accumulation of Labelled Platelets in Experimental Thrombi

Thrombi were induced by electrocoagulation techniques described in Thakur et al. Thrombosis, Res. 9, 345–347, 1976, in the femoral vein of a dog. One hour following this procedure, 400 μCi of the indium 111 labelled platelets in plasma (4 ml) prepared in Example 4 were administered to the animal intravenously. Within 40 min. after platelet administration, thrombi were clearly detectable by gamma-camera imaging. After 3 hrs. following platelet injection the thrombus of each of the animals was dissected, weighed and the radioactivity therein counted. The radioactivity of the thrombi at 3 hrs. post-platelet injection, was 59.4×greater than in the equal weight of animal's blood.

EXAMPLE 10

Labelling Leukocytes

The amount of 30 mls of hepartinized venous blood was drawn from healthy human volunteers. Leukocytes were separated from the blood as described in Thakur et al., J. Lab. Clin. Med., 89 217–228 (1977). A 1 ml plasma solution containing 20×10$^6$ leukocytes was incubated with 50 μl of the saline solution containing 50 μg of the indium-111 complex prepared in Example 2 (radioactivity 100 μCi). The incubation was carried out at room temperature for 15 min. and the resulting mixture was centrifuged. After centrifuging, the activities of the supernatant and the labelled cells were measured. It was found that the radioactivity of the labelled cells was approximately 70% of the radioactivity of the indium complex incorporated into the cell.

EXAMPLE 11

The same procedure as used in Example 10 was utilized for labelling red blood cells and leukocytes. This procedure utilized various radioactive concentrations of indium-111 pyrithione complex prepared in Example 2.

The results of various concentrations of the radioactive complex in labelling the leukocyte cells is given in the following Table. In this Table, the results of various experiments with regard to leukocytes and red blood cells (RBC) is given. The results given for each experiment is calculated in the percent of radioactivity incorporated into the cell. This percent radioactivity incorporated was determined by expressing by a percent the amount of radioactivity measured for the labelled cells as against the amount of radioactivity used to label the cells, i.e. the amount of radioactivity in the complex. The complex is designated in the Table as Merc. The anticoagulant is the medium used in preventing coagulation when the cells were prepared. The results were as follows:

TABLE 1

Leukocyte and Red Blood Cell Labeling in Plasma

Influence of Merc concentration
15 Minutes incubation at 22° C.
Leukocyte and RBC concentration 20 × 10$^6$ leukocytes/ml
% Radioactivity incorporated

| μg/ml | Leukocytes I | II | III | RBC* I | Leuckocytes** I | II | RBC** I | II |
|---|---|---|---|---|---|---|---|---|
| 2.5 | 8.7 | — | — | 8.7 | 10.5 | — | 5.6 | — |
| 5 | — | — | — | — | 26.1 | — | 7.7 | — |
| 7.5 | 14.5 | — | — | — | 40.6 | — | 8.7 | — |
| 10 | — | — | — | — | 65.1 | — | 10.4 | — |
| 12.5 | 24.3 | — | — | — | 72.8 | 63.9 | 12.1 | 8.7 |
| 17.5 | 28.7 | — | — | — | — | — | — | 12.1 |
| 25 | 37.5 | 79.4 | 49.2 | 5.7 | — | 72.6 | — | 13.3 |
| 37.5 | 45.2 | 83.0 | 60.4 | 6.9 | — | 76.9 | — | 13.0 |
| 50 | — | 83.0 | 64.3 | 8.3 | — | 72.0 | — | 9.2 |
| 62.5 | — | 82.0 | 63.1 | 8.8 | — | 32.7 | — | — |
| 75 | — | 74.3 | 60.2 | — | — | — | — | — |
| 87.5 | — | 71.2 | — | — | — | — | — | — |
| 100 | — | — | 54.2 | — | — | — | — | — |

*Anticoagulant - heparin 6 I.V./ml
**Anticoagulant - 3.8 Na Citrate - pH 7.4 1:6

EXAMPLE 12

The same procedure for labelling leukocytes and red blood cells as in Example 11 was used except that incubation was carried out for 15 min. in a medium which consisted of aqueous solution containing 0.9% by weight sodium chloride rather than in plasma. The results are as follows:

TABLE 2

Leukocytes and RBC Labeling in 0.9% NaCl

Influence of Merc concentration
15 Minute Incubation at 22° C.
Leukocytes and RBC conc. 20 × 10$^6$/ml
% Radioactivity incorporated
6 I.V./ml heparin as anticoagulent

| μg/ml | Leukocytes I | II | III | RBC I | II |
|---|---|---|---|---|---|
| 2.5 | 98.4 | 97.9 | 96.6 | 65.7 | 91.4 |
| 5 | 98.4 | 97.9 | — | 11.6 | — |
| 7.5 | 95.2 | 96.4 | — | 6.7 | — |
| 10 | 87.5 | 95 | — | 5.6 | — |
| 12.5 | 83.5 | 93.7 | 87.4 | 5.7 | 14.1 |
| 17.5 | — | — | — | — | 8.5 |
| 25 | — | — | 51.1 | — | 7.4 |
| 37.5 | — | — | 37 | — | 7.9 |
| 50 | — | — | 27.1 | — | — |

EXAMPLE 13

Lymphocytes were labelled by the procedure of Example 11 utilizing plasma as the incubation medium.

EXAMPLE 14

Leukocytes were labelled with indium-111 pyrithione complex in an aqueous solution containing 0.9% by weight of sodium chloride as described in Example 12. 1 ml of this leukocyte labelled suspension which had a radioactivity of 500 μCi was administered intravenously into dogs which previously had a sterile abcess induced in their right hind legs. The sterile abscess was induced by the procedure of Thakur et al., J. Lab. Clin. Med., 89, 217–228, 1977. The leukocytes which were labelled were intravenously injected 24 hours after the induction of the sterile abscesses. The abscesses were imaged 18 hrs. later and were clearly detected.

EXAMPLE 15

Preparation of the technetium-99m pyrithione complex

Various test tubes were prepared containing an aqueous acetate buffer solution at different pH's ranging from 3.5 to 7.4. Each of these test tubes had 2 ml of one of these buffer solutions. To each of these test tubes, there were added 10 μl of a 10 mg/ml stannous chloride solution in ethanol. After this addition, there was added 10 μl of pyrithione (concentration 1 mg/ml) in saline. After this addition, there was added a solution of technetium 99-m pertechnetate in saline which solution had a radioactivity of approximately 200 μCi. The resulting solution was allowed to stand at room temperature for 5 minutes to form the technetium complex of pyrithione, i.e. tris-[1-hydroxy-2(1H)pyridine-thionato-O-S]-technetium-99m.

Each of the test tubes containing the technetium-99m complex of pyrithione was treated as follows. The contents of the test tube was extracted in two equal volumes of chloroform and the chloroform extracts were combined. The radioactivity of the technetium 99-pyrithione complex in chloroform was measured and the percentage of radioactivity in the extract as compared to the original radioactivity was determined. From the results, the activity was highest at a pH of 4. The percentage of radioactivity of the complex formed at this pH was above 70%. To obtain the complex, the chloroform extract was evaporated to dryness by placing the test tube in a boiling water bath while allowing a gentle stream of nitrogen to blow over the solution. The resulting dry technetium-99m-pyrithione complex had a radioactive of approximately 70% of the original radioactivity of the technetium 99m utilized in labelling. To prepare the aqueous solution of this compound, the complex was dissolved in an aqueous solution containing sodium chloride. The radioactive complex in this sodium chloride solution was utilized to label platelets in accordance with the procedure of Example 5.

EXANPLE 16

Preparation of Ruthenium-103 Complex of Pyrithione

In preparing these complexes, various test tubes were prepared, each containing 2 ml of various buffer solutions having pH's ranging from 3.5 to 7.5. This was done to study the effects of various pH's in forming the complexes. In each of these test tubes, there was added approximately 50 μl (50 μCi) of an aqueous ruthenium-103 chloride solution. After the addition of the aqueous ruthenium-103 solution, there was added to each of the test tubes 100 μl of an aqueous solution containing 1 mg/ml pyrithione. This solution contained 0.9% by weight sodium chloride. Each test tube was then heated at 90° C. in a water bath for 15 min. and allowed to cool. Each of the test tubes which contained the ruthenium-103 complex of pyrithione, i.e. tris-[1-hydroxy(2)1H-pyridine-thionato-O,S]ruthenium-103. By the procedure of Example 15, the complex from each of the test tubes was extracted from chloroform and the percentage radioactivity determined. The highest percent of radioactivity was determined for the complex formed at approximately 7.4. The chloroform layer was evaporated and the dry complex was then dissolved in an aqueous solution containing 0.9% by weight of sodium chloride. This solution was used for cell labelling in accordance with Example 4.

I claim:

1. A process for imaging blood cells comprising intravenously injecting an effective amount of a composition containing the blood cells to be imaged which have been radioactively labelled by means of a complex of a radioactive metal selected from the group consisting of technetium, indium, ruthenium or gallium, with a compound of the formula:

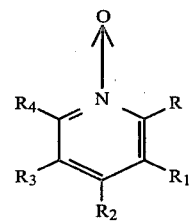

wherein R is an electron denoting or an electron withdrawing group; and $R_1$, $R_2$, $R_3$ and $R_4$ and independently halogen, methoxy, ethoxy, hydrogen—$(CH_2)_n$—COOH, methyl or ethyl; and n is 0 or 1 in a carrier suitable for intravenous injection and scanning the area to be imaged with a scintiscanning means.

2. The process of claim 1 wherein said radioactive metal is ruthenium.

3. The process of claim 2 wherein said compound is pyrithione.

4. The process of claim 1 wherein said radioactive metal is technetium is 99m.

5. The process of claim 4 wherein said compound is pyrithione.

6. The process of claim 1 wherein said metal is gallium.

7. The process of claim 6 wherein said metal is indium.

8. The process of claim 7 wherein said complex is a complex of indium-111 and pyrithione.

9. The process of claim 8 wherein said cells are platelets.

10. The process of claim 8 wherein said cells are red blood cells.

11. The process of claim 8 wherein said cells are leukocytes.

12. The process of claim 8 wherein said cells are lymphocytes.

13. A process for labelling blood cells comprising treating the blood cells to be labelled with a complex of a radioactive metal selected from the group consisting of technetium, indium, gallium or ruthenium with a compound of the formula:

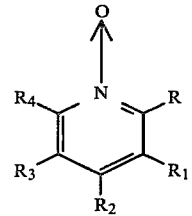

wherein R is an electron denoting or electron withdrawing group; and $R_1$, $R_2$, $R_3$ and $R_4$ are independently halogen, methoxy, ethoxy, hydrogen—$(CH_2)_2$—COOH, methyl or ethyl; and n is 0 or 1.

14. The process of claim 13 wherein said radioactive metal is indium-111.

15. The process of claim 14 wherein said compound is pyrithione.

16. The process of claim 15 wherein said treatment is carried out in a reaction medium containing plasma.

17. The process of claim 16 wherein said cells are platelets.

18. The process of claim 16 wherein said cells are leukocytes.

19. The process of claim 18 wherein said cells are red blood cells.

20. A radioactive complex of a radioactive metal selected from the group consisting of indium, technetium, gallium and ruthenium with a compound of the formula

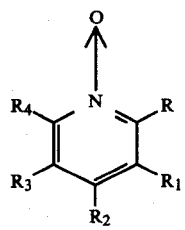

wherein R is an electron denoting or an electron withdrawing group; and $R_1$, $R_2$, $R_3$ and $R_4$ are independently halogen methoxy, ethoxy, hydrogen, $-(CH_2)_n-COOH$, methyl or ethyl; and n is 0 or 1.

21. The complex of claim 20 wherein said complex has a radioactivity of from 100 $\mu$Ci to 50 mCi.

22. The chelate of claim 20 wherein said complex is a complex of indium-111 and pyrithione.

23. A radioactive composition comprising a solution of radioactive chelates of radioactive metal selected from the group consisting of technetium, indium, ruthenium and gallium and a compound of the formula

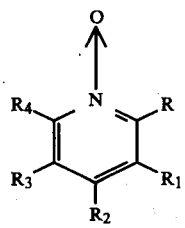

wherein R is an electron denoting or an electron withdrawing group; and $R_1$, $R_2$, $R_3$ and $R_4$ are independently halogen methoxy, ethoxy, hydrogen, $-(CH_2)_n-COOH$, methyl or ethyl; and n is 0 or 1 in a solvent.

24. The composition of claim 23 wherein the solution has a radioactivity of from 100 $\mu$Ci to 50 mCi per ml of said solution.

25. The composition of claim 24 wherein said complex is a complex of indium-111 with pyrithione.

26. A composition suitable for intravenous injection comprising a solution containing blood cells labelled with a complex of a radioactive metal selected from the group consisting of technetium, indium, rubidium, and ruthenium and a compound of the formula

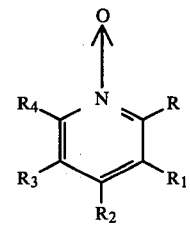

wherein R is an electron denoting an electron withdrawing group; and $R_1$, $R_2$, $R_3$ and $R_4$ are independently halogen, methoxy, ethoxy, hydrogen, $-(CH_2)_n-COOH$, methyl or ethyl; and n is 0 or 1 said blood cells being dissolved in a solvent suitable for intravenous injection.

27. The composition of claim 26 wherein said complex is a complex of indium-111 and pyrithione.

28. The composition of claim 27 wherein said blood cells are present in the solution in an amount of from $0.5 \times 10^8$ cells to $200 \times 10^8$ cells and the solution has a radioactivity of 100 $\mu$Ci to 50 mCi.

29. The composition of claim 28 wherein said composition is in a single injectable dose of from 1 ml to 10 ml.

30. A process for imaging blood cells comprising intravenously injecting an effective amount of a composition containing the blood cells to be imaged which have been radioactively labelled by means of a complex of a radioisotope of indium with pyrithione or its alkali metal salts and a carrier suitable for intravenous injection and scanning the area to be imaged with a scintiscanning means.

31. The process of claim 30 wherein said composition has a radioactivity of 100 $\mu$Ci to 50 mCi.

32. The process of claim 30 wherein said complex is a complex of indium-111 and pyrithione.

33. A composition suitable for intravenous injection comprising a solution containing blood cells labelled with a complex of a radioisotope of indium and pyrithione or its alkali metal salts, said blood cells being dissolved in a solvent suitable for intravenous injection.

34. The composition of claim 33 wherein said blood cells are present in the solution in an amount of from $0.5 \times 10^8$ cells to $200 \times 10^8$ cells and the solution has a radioactivity of 100 $\mu$Ci to 50 Ci.

35. The composition of claim 34 wherein said composition is in a single injectable dose of from 1 ml to 10 ml.

36. The novel processes, intermediates, compositions and methods as disclosed herein.

* * * * *